US012667311B2

(12) United States Patent
Sowards et al.

(10) Patent No.: US 12,667,311 B2
(45) Date of Patent: Jun. 30, 2026

(54) EXTENDED FIBER OPTIC SENSING SYSTEM

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert Mclaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 917 days.

(21) Appl. No.: 17/721,333

(22) Filed: Apr. 14, 2022

(65) Prior Publication Data

US 2022/0330891 A1 Oct. 20, 2022

Related U.S. Application Data

(60) Provisional application No. 63/175,449, filed on Apr. 15, 2021.

(51) Int. Cl.
*A61B 5/00* (2006.01)
*A61B 5/01* (2006.01)
(Continued)

(52) U.S. Cl.
CPC .............. *A61B 5/6847* (2013.01); *A61B 5/01* (2013.01); *A61B 5/0261* (2013.01);
(Continued)

(58) Field of Classification Search
CPC .... G02B 6/02042; G01D 5/3538; A61B 5/01; A61B 5/0261; A61B 5/14552;
(Continued)

(56) References Cited

U.S. PATENT DOCUMENTS

| | | |
|---|---|---|
| 3,493,288 A | 2/1970 | Oltman et al. |
| 4,768,855 A | 9/1988 | Nishi et al. |

(Continued)

FOREIGN PATENT DOCUMENTS

| | | |
|---|---|---|
| CA | 3025240 A1 | 11/2017 |
| DE | 102016109601 A1 | 11/2017 |

(Continued)

OTHER PUBLICATIONS

U.S. Appl. No. 17/731,129, filed Apr. 27, 2022 Final Office Action dated Aug. 27, 2025.

(Continued)

*Primary Examiner* — Daniel Petkovsek
(74) *Attorney, Agent, or Firm* — Rutan & Tucker LLP

(57) ABSTRACT

An elongate multi-core optical fiber instrument for insertion within a patient body includes a set of first optical fiber cores extending along a first sensing region of the multi-core optical fiber instrument, where each first optical fiber core includes a set of first sensors disposed along the first region and a set of second optical fiber cores extending along a second sensing region of the multi-core optical fiber instrument, where each second optical fiber core includes a set of second sensors disposed along the second sensing region. The first sensing region is located distal the second sensing region, and the first optical fiber cores extend along the second sensing region. Also disclosed is a console for providing an incident light signal to the multi-core optical fiber instrument, receiving reflected light signals from the sensors, and determining a parameter experienced by instrument in accordance with the reflected light signals.

27 Claims, 6 Drawing Sheets

(51) Int. Cl.

| | | |
|---|---|---|
| *A61B 5/026* | (2006.01) | |
| *A61B 5/1455* | (2006.01) | |
| *A61B 5/1459* | (2006.01) | |
| *A61B 34/20* | (2016.01) | |
| *G01D 5/353* | (2006.01) | |
| *G02B 6/02* | (2006.01) | |

(52) U.S. Cl.
CPC ........ *A61B 5/14552* (2013.01); *A61B 5/1459* (2013.01); *A61B 5/742* (2013.01); *A61B 34/20* (2016.02); *G01D 5/3538* (2013.01); *G02B 6/02042* (2013.01); *A61B 2034/2061* (2016.02)

(58) Field of Classification Search
CPC ..... A61B 5/1459; A61B 5/6847; A61B 5/742; A61B 34/20; A61B 2034/2061
See application file for complete search history.

(56) References Cited

U.S. PATENT DOCUMENTS

| | | | |
|---|---|---|---|
| 4,777,955 A | | 10/1988 | Brayton et al. |
| 4,813,429 A | | 3/1989 | Eshel et al. |
| 4,898,176 A | | 2/1990 | Petre |
| 4,984,581 A | | 1/1991 | Stice |
| 5,099,845 A | | 3/1992 | Besz et al. |
| 5,163,935 A | | 11/1992 | Black et al. |
| 5,178,153 A | | 1/1993 | Einzig |
| 5,207,672 A | | 5/1993 | Roth et al. |
| 5,211,165 A | | 5/1993 | Dumoulin et al. |
| 5,220,703 A | | 6/1993 | Kanayama et al. |
| 5,275,151 A | | 1/1994 | Shockey et al. |
| 5,295,212 A | | 3/1994 | Morton et al. |
| 5,423,321 A | | 6/1995 | Fontenot |
| 5,454,807 A | | 10/1995 | Lennox et al. |
| 5,517,997 A | | 5/1996 | Fontenot |
| 5,599,492 A | | 2/1997 | Engelson |
| 5,622,170 A | | 4/1997 | Schulz |
| 5,633,494 A | | 5/1997 | Danisch |
| 5,693,043 A | * | 12/1997 | Kittrell .............. A61B 1/00096 |
| | | | 606/15 |
| 5,740,808 A | | 4/1998 | Panescu et al. |
| 5,827,313 A | | 10/1998 | Ream |
| 5,872,879 A | | 2/1999 | Hamm |
| 5,873,842 A | | 2/1999 | Brennen et al. |
| 5,879,306 A | | 3/1999 | Fontenot et al. |
| 5,906,579 A | | 5/1999 | Vander Salm et al. |
| 5,957,831 A | | 9/1999 | Adair |
| 6,035,229 A | | 3/2000 | Silverstein et al. |
| 6,069,698 A | | 5/2000 | Ozawa et al. |
| 6,081,741 A | | 6/2000 | Hollis |
| 6,178,346 B1 | | 1/2001 | Amundson et al. |
| 6,208,887 B1 | | 3/2001 | Clarke |
| 6,210,362 B1 | | 4/2001 | Ponzi |
| 6,258,118 B1 | | 7/2001 | Baum et al. |
| 6,319,227 B1 | | 11/2001 | Mansouri-Ruiz |
| 6,343,227 B1 | | 1/2002 | Crowley |
| 6,371,928 B1 | | 4/2002 | Mcfann et al. |
| 6,398,721 B1 | | 6/2002 | Nakamura et al. |
| 6,485,482 B1 | | 11/2002 | Belef |
| 6,563,105 B2 | | 5/2003 | Seibel et al. |
| 6,564,089 B2 | | 5/2003 | Izatt et al. |
| 6,593,884 B1 | | 7/2003 | Gilboa et al. |
| 6,597,941 B2 | | 7/2003 | Fontenot et al. |
| 6,619,857 B2 | | 9/2003 | Miyake |
| 6,650,923 B1 | | 11/2003 | Lesh et al. |
| 6,685,666 B1 | | 2/2004 | Fontenot |
| 6,687,010 B1 | | 2/2004 | Horii et al. |
| 6,690,966 B1 | | 2/2004 | Rava et al. |
| 6,701,181 B2 | | 3/2004 | Tang et al. |
| 6,711,426 B2 | | 3/2004 | Benaron et al. |
| 6,816,743 B2 | | 11/2004 | Moreno et al. |
| 6,892,090 B2 | | 5/2005 | Verard et al. |
| 6,895,267 B2 | | 5/2005 | Panescu et al. |
| 6,975,803 B2 | | 12/2005 | Koide et al. |

| | | | |
|---|---|---|---|
| 7,043,287 B1 | | 5/2006 | Khalil et al. |
| 7,132,645 B2 | | 11/2006 | Kom |
| 7,273,056 B2 | | 9/2007 | Wilson et al. |
| 7,344,533 B2 | | 3/2008 | Pearson et al. |
| 7,366,562 B2 | | 4/2008 | Dukesherer et al. |
| 7,366,563 B2 | | 4/2008 | Kleen et al. |
| 7,396,354 B2 | | 7/2008 | Rychnovsky et al. |
| 7,406,346 B2 | | 7/2008 | Kleen et al. |
| 7,515,265 B2 | | 4/2009 | Alfano et al. |
| 7,532,920 B1 | | 5/2009 | Ainsworth et al. |
| 7,587,236 B2 | | 9/2009 | Demos et al. |
| 7,603,166 B2 | | 10/2009 | Casscells et al. |
| 7,699,855 B2 | | 4/2010 | Anderson et al. |
| 7,729,735 B1 | | 6/2010 | Burchman |
| 7,757,695 B2 | | 7/2010 | Wilson et al. |
| 7,758,499 B2 | | 7/2010 | Adler |
| 7,840,253 B2 | | 11/2010 | Tremblay et al. |
| 7,992,573 B2 | | 8/2011 | Wilson et al. |
| 8,032,200 B2 | | 10/2011 | Tearney et al. |
| 8,054,469 B2 | | 11/2011 | Nakabayashi et al. |
| 8,060,187 B2 | | 11/2011 | Marshik-Geurts et al. |
| 8,073,517 B1 | | 12/2011 | Burchman |
| 8,078,261 B2 | | 12/2011 | Imam |
| 8,182,433 B2 | | 5/2012 | Leo et al. |
| 8,187,189 B2 | | 5/2012 | Jung et al. |
| 8,197,494 B2 | | 6/2012 | Jaggi et al. |
| 8,267,932 B2 | | 9/2012 | Baxter et al. |
| 8,369,932 B2 | | 2/2013 | Cinbis et al. |
| 8,388,541 B2 | | 3/2013 | Messerly et al. |
| 8,571,640 B2 | | 10/2013 | Holman |
| 8,597,315 B2 | | 12/2013 | Snow et al. |
| 8,622,935 B1 | | 1/2014 | Leo |
| 8,700,358 B1 | | 4/2014 | Parker, Jr. |
| 8,781,555 B2 | | 7/2014 | Burnside et al. |
| 8,798,721 B2 | | 8/2014 | Dib |
| 8,968,331 B1 | | 3/2015 | Sochor |
| 8,979,871 B2 | | 3/2015 | Tyc et al. |
| 9,119,551 B2 | | 9/2015 | Qi et al. |
| 9,186,046 B2 | | 11/2015 | Ramamurthy et al. |
| 9,339,206 B2 | | 5/2016 | Grunwald |
| 9,339,221 B1 | | 5/2016 | Heaton, II et al. |
| 9,345,510 B2 | | 5/2016 | Patel et al. |
| 9,360,630 B2 | | 6/2016 | Jenner et al. |
| 9,549,685 B2 | | 1/2017 | Cox et al. |
| 9,560,954 B2 | | 2/2017 | Jacobs et al. |
| 9,572,492 B2 | | 2/2017 | Simpson et al. |
| 9,622,706 B2 | | 4/2017 | Dick et al. |
| 9,645,326 B1 | | 5/2017 | Sausse et al. |
| 9,649,048 B2 | | 5/2017 | Cox et al. |
| 9,678,275 B1 | | 6/2017 | Griffin |
| 9,678,284 B2 | | 6/2017 | Coggi et al. |
| 9,737,213 B1 | | 8/2017 | Heaton, II et al. |
| 9,872,978 B1 | | 1/2018 | Zaborsky et al. |
| 10,231,643 B2 | | 3/2019 | Grunwald |
| 10,231,753 B2 | | 3/2019 | Burnside et al. |
| 10,258,240 B1 | | 4/2019 | Eberle et al. |
| 10,265,133 B2 | | 4/2019 | McClellan |
| 10,327,830 B2 | | 6/2019 | Grant et al. |
| 10,349,890 B2 | | 7/2019 | Misener et al. |
| 10,448,837 B2 | | 10/2019 | Manzke et al. |
| 10,492,876 B2 | | 12/2019 | Anastassiou et al. |
| 10,551,245 B2 | | 2/2020 | Do et al. |
| 10,568,586 B2 | | 2/2020 | Begin et al. |
| 10,603,126 B2 | | 3/2020 | Karguth et al. |
| 10,620,386 B2 | | 4/2020 | Van Der Mark et al. |
| 10,631,718 B2 | | 4/2020 | Petroff et al. |
| 10,687,891 B2 | | 6/2020 | Belhe et al. |
| 10,932,670 B2 | | 3/2021 | Smith et al. |
| 10,939,889 B2 | | 3/2021 | Flexman et al. |
| 10,992,078 B2 | | 4/2021 | Thompson et al. |
| 10,992,079 B2 | | 4/2021 | Stats et al. |
| 11,000,207 B2 | | 5/2021 | Burnside et al. |
| 11,000,265 B1 | | 5/2021 | Ryu et al. |
| 11,103,321 B2 | | 8/2021 | Braun et al. |
| 11,123,047 B2 | | 9/2021 | Jaffer et al. |
| 11,259,892 B2 | | 3/2022 | Hufford et al. |
| 11,284,916 B2 | | 3/2022 | Patel et al. |
| 11,369,342 B2 | | 6/2022 | Irisawa |
| 11,382,653 B2 | | 7/2022 | Patel et al. |

(56)  References Cited

U.S. PATENT DOCUMENTS

| | | |
|---|---|---|
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,630,009 B2 | 4/2023 | Misener et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 12,038,338 B2 | 7/2024 | Misener et al. |
| 12,048,478 B2 | 7/2024 | Tegg et al. |
| 12,089,815 B2 | 9/2024 | Sowards et al. |
| 2002/0019627 A1 | 2/2002 | Maguire et al. |
| 2002/0087206 A1 | 7/2002 | Hirschberg et al. |
| 2002/0166190 A1 | 11/2002 | Miyake et al. |
| 2002/0188285 A1 | 12/2002 | Brown |
| 2002/0198457 A1 | 12/2002 | Tearney et al. |
| 2003/0045798 A1 | 3/2003 | Hular et al. |
| 2003/0092995 A1 | 5/2003 | Thompson |
| 2004/0039274 A1 | 2/2004 | Benaron et al. |
| 2004/0111020 A1 | 6/2004 | Long |
| 2004/0111147 A1 | 6/2004 | Rabkin et al. |
| 2004/0242995 A1 | 12/2004 | Maschke |
| 2004/0247268 A1 | 12/2004 | Ishihara et al. |
| 2004/0260182 A1 | 12/2004 | Zuluaga et al. |
| 2005/0033264 A1 | 2/2005 | Redinger |
| 2005/0113719 A1 | 5/2005 | Saadat |
| 2005/0272975 A1 | 12/2005 | McWeeney et al. |
| 2006/0013523 A1 | 1/2006 | Childlers et al. |
| 2006/0030753 A1 | 2/2006 | Boutillette et al. |
| 2006/0036164 A1 | 2/2006 | Wilson et al. |
| 2006/0069305 A1 | 3/2006 | Couvillon et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0225563 A1 | 9/2007 | Ogino |
| 2007/0253673 A1 | 11/2007 | Nielsen et al. |
| 2007/0265503 A1 | 11/2007 | Schlesinger et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0270729 A1 | 10/2009 | Corbucci et al. |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0274235 A1 | 10/2010 | Mihajlovic et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0116161 A1 | 5/2012 | Nieman et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0073950 A1 | 3/2014 | Akui et al. |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0180087 A1 | 6/2014 | Millett et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0268167 A1 | 9/2014 | Friedman et al. |
| 2014/0275997 A1 | 9/2014 | Chopra et al. |
| 2014/0318825 A1 | 10/2014 | Erb et al. |
| 2014/0323887 A1 | 10/2014 | Anderson et al. |
| 2014/0378945 A1 | 12/2014 | Beri |
| 2015/0029511 A1* | 1/2015 | 'T Hooft ............ G01B 9/02004<br>356/477 |
| 2015/0031987 A1 | 1/2015 | Pameijer et al. |
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0272445 A1 | 10/2015 | Rozental et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |

(56) References Cited

U.S. PATENT DOCUMENTS

| | | |
|---|---|---|
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290542 A1 | 10/2017 | Chandrasoma |
| 2017/0296037 A1 | 10/2017 | Yoshino |
| 2017/0303824 A1 | 10/2017 | Schlesinger et al. |
| 2017/0311924 A1 | 11/2017 | Sudol |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1 | 4/2018 | Patil et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0317751 A1 | 11/2018 | Kuboi et al. |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0192818 A1 | 6/2019 | Koda et al. |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0022587 A1 | 1/2020 | Glover et al. |
| 2020/0046434 A1 | 2/2020 | Graetzel et al. |
| 2020/0060718 A1 | 2/2020 | Patel et al. |
| 2020/0069192 A1 | 3/2020 | Sanborn et al. |
| 2020/0093353 A1 | 3/2020 | Tezuka et al. |
| 2020/0155073 A1 | 5/2020 | Hwang et al. |
| 2020/0170724 A1 | 6/2020 | Flatt et al. |
| 2020/0188036 A1* | 6/2020 | Ding .................. A61B 17/7074 |
| 2020/0238051 A1 | 7/2020 | Hwang et al. |
| 2020/0261720 A1 | 8/2020 | Danitz et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0113274 A1 | 4/2021 | Bydlon et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0039744 A1 | 2/2022 | Koenig |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0361762 A1 | 11/2022 | Lalancette et al. |
| 2023/0082991 A1 | 3/2023 | Sowards et al. |
| 2023/0149080 A1 | 5/2023 | Wong et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |
| 2025/0249208 A1 | 8/2025 | Sowards et al. |
| 2025/0288366 A1 | 9/2025 | Misener et al. |
| 2026/0076763 A1 | 3/2026 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 2809249 B1 | 12/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |

(56)                    References Cited

FOREIGN PATENT DOCUMENTS

| WO | 2023043947 A1 | 3/2023 |
|----|---------------|--------|
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

U.S. Appl. No. 17/731,155, filed Apr. 27, 2022 Non-Final Office Action dated Jul. 15, 2025.
U.S. Appl. No. 17/849,447, filed Jun. 24, 2022 Ex Parte Quayle Action dated Sep. 4, 2025.
U.S. Appl. No. 17/863,211, filed Jul. 12, 2022 Advisory Action dated Sep. 11, 2025.
U.S. Appl. No. 17/945,875, filed Sep. 15, 2022 Notice of Allowance dated Jul. 21, 2025.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/191,551, filed Mar. 3, 2021 Notice of Allowance dated Nov. 8, 2024.
U.S. Appl. No. 17/689,773, filed Mar. 8, 2022 Advisory Action dated Nov. 1, 2024.
U.S. Appl. No. 17/689,773, filed Mar. 8, 2022 Notice of Allowance dated Jan. 15, 2025.
U.S. Appl. No. 17/696,675, filed Mar. 16, 2022 Advisory Action dated Feb. 6, 2025.
U.S. Appl. No. 17/696,675, filed Mar. 16, 2022 Final Office Action dated Dec. 5, 2024.
U.S. Appl. No. 17/725,394, filed Apr. 20, 2022 Non-Final Office Action dated Nov. 19, 2024.
U.S. Appl. No. 17/731,155, filed Apr. 27, 2022 Final Office Action dated Jan. 24, 2025.
U.S. Appl. No. 17/849,447, filed Jun. 24, 2022 Non-Final Office Action dated Jan. 17, 2025.
U.S. Appl. No. 17/849,447, filed Jun. 24, 2022 Restriction Requirement dated Apr. 15, 2024.
U.S. Appl. No. 17/863,211, filed Jul. 12, 2022 Non-Final Office Action dated Jan. 29, 2025.
U.S. Appl. No. 17/863,211, filed Jul. 12, 2022 Restriction Requirement dated Nov. 15, 2024.
U.S. Appl. No. 18/141,289, filed Apr. 28, 2023 Notice of Allowance dated Jan. 10, 2025.
U.S. Appl. No. 18/607,165, filed Mar. 15, 2024 Non-Final Office Action dated Jan. 15, 2025.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide- coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/187,536, filed Feb. 26, 2021 Final Office Action dated Jul. 2, 2024.
U.S. Appl. No. 17/689,773, filed Mar. 8, 2022 Non-Final Office Action dated Mar. 19, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.

U.S. Appl. No. 17/725,394, filed Apr. 20, 2022 Non-Final Office Action dated Jun. 17, 2024.
U.S. Appl. No. 17/849,447, filed Jun. 24, 2022 Non-Final Office Action dated Apr. 10, 2024.
U.S. Appl. No. 18/524,620, filed Nov. 30, 2023 Non-Final Office Action dated Jun. 18, 2024.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
US17/185,777 filed Feb. 25, 2021 Notice of Allowance dated Jun. 10, 2022.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
U.S. Appl. No. 17/529,022, filed Nov. 17, 2021 Notice of Allowance dated Jan. 2, 2025.
U.S. Appl. No. 17/529,022, filed Nov. 17, 2021 Restriction Requirement dated May 2, 2024.
U.S. Appl. No. 17/696,675, filed Mar. 16, 2022 Notice of Allowance dated Jun. 17, 2025.
U.S. Appl. No. 17/717,919, filed Apr. 11, 2022 Non-Final Office Action dated Jul. 1, 2025.
U.S. Appl. No. 17/717,919, filed Apr. 11, 2022 Restriction Requirement dated Apr. 23, 2025.
U.S. Appl. No. 17/725,394, filed Apr. 20, 2022 Advisory Action dated Jun. 5, 2025.
U.S. Appl. No. 17/725,394, filed Apr. 20, 2022 Final Office Action dated Mar. 27, 2025.
U.S. Appl. No. 17/725,394, filed Apr. 20, 2022 Non-Final Office Action dated Jun. 25, 2025.
U.S. Appl. No. 17/731,129, filed Apr. 27, 2022 Non-Final Office Action dated Apr. 28, 2025.
U.S. Appl. No. 17/731,129, filed Apr. 27, 2022 Restriction Requirement dated Feb. 28, 2025.
U.S. Appl. No. 17/731,155, filed Apr. 27, 2022 Advisory Action dated Apr. 3, 2025.
U.S. Appl. No. 17/849,447, filed Jun. 24, 2022 Final Office Action dated May 7, 2025.
U.S. Appl. No. 17/863,211, filed Jul. 12, 2022 Final Office Action dated Jun. 3, 2025.
U.S. Appl. No. 17/945,875, filed Sep. 15, 2022 Non-Final Office Action dated Feb. 27, 2025.
U.S. Appl. No. 18/075,280, filed Dec. 5, 2022 Non-Final Office Action dated Jun. 11, 2025.
U.S. Appl. No. 18/075,280, filed Dec. 5, 2022 Restriction Requirement dated Mar. 28, 2025.
U.S. Appl. No. 18/607,165, filed Mar. 15, 2024 Notice of Allowance dated Apr. 3, 2025.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.

(56) References Cited

OTHER PUBLICATIONS

U.S. Appl. No. 17/697,895, filed Mar. 17, 2022 Final Office Action dated Aug. 16, 2023.

U.S. Appl. No. 17/697,895, filed Mar. 17, 2022 Non Final Office Action dated Jun. 14, 2023.

PCT/US2023/015536 filed Mar. 17, 2023 International Preliminary Report on Patentability dated Sep. 10, 2024.

PCT/US2023/018076 filed Apr. 10, 2023 International Preliminary Report on Patentability dated Oct. 8, 2024.

U.S. Appl. No. 17/187,536, filed Feb. 26, 2021 Advisory Action dated Oct. 9, 2024.

U.S. Appl. No. 17/187,536, filed Feb. 26, 2021 Notice of Allowance dated Oct. 29, 2024.

U.S. Appl. No. 17/191,551, filed Mar. 3, 2021 Non-Final Office Action dated Aug. 16, 2024.

U.S. Appl. No. 17/529,022, filed Nov. 17, 2021 Non-Final Office Action dated Sep. 30, 2024.

U.S. Appl. No. 17/535,406, filed Nov. 24, 2021 Final Office Action dated Aug. 1, 2024.

U.S. Appl. No. 17/535,406, filed Nov. 24, 2021 Notice of Allowance dated Oct. 23, 2024.

U.S. Appl. No. 17/689,773, filed Mar. 8, 2022 Final Office Action dated Aug. 1, 2024.

U.S. Appl. No. 17/731,155, filed Apr. 27, 2022 Non-Final Office Action dated Aug. 22, 2024.

U.S. Appl. No. 17/849,447, filed Jun. 24, 2022 Advisory Action dated Oct. 24, 2024.

U.S. Appl. No. 17/849,447, filed Jun. 24, 2022 Final Office Action dated Aug. 8, 2024.

U.S. Appl. No. 18/141,289, filed Apr. 28, 2023 Non-Final Office Action dated Sep. 28, 2024.

U.S. Appl. No. 18/524,620, filed Nov. 30, 2023 Notice of Allowance dated Sep. 12, 2024.

PCT/US2022/043698 filed Sep. 15, 2022 International Search Report and Written Opinion dated Dec. 19. 2022.

U.S. Appl. No. 17/967,794, filed Oct. 17, 2022 Notice of Allowance dated Feb. 15, 2023.

PCT/US2021 /059755 filed Nov. 17, 2021 International Search Report and Written Opinion dated Apr. 29, 2022.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

PCT/US2021/020732 filed Mar. 3, 2021 International Search Report and Written Opinion dated Jul. 5, 2021.

PCT/US2021/060849 filed Nov. 24, 2021 International Search Report and Written Opinion dated Mar. 9, 2022.

U.S. Appl. No. 17/185,777, filed Feb. 25, 2021 Non-Final Office Action dated Feb. 9, 2022.

PCT/US2022/024934 filed Apr. 14, 2022 International Search Report and Written Opinion dated Jul. 18. 2022.

PCT/US2023/020042 filed Apr. 26, 2023 International Search Report and Written Opinion dated Sep. 26, 2023.

PCT/US2023/025757 filed Jun. 20, 2023 International Search Report and Written Opinion dated Sep. 11, 2023.

PCT/US2023/027527 filed Jul. 12, 2023 International Search Report and Written Opinion dated Oct. 16, 2023.

U.S. Appl. No. 17/187,536, filed Feb. 26, 2021 Advisory Action dated Nov. 21, 2023.

U.S. Appl. No. 17/187,536, filed Feb. 26, 2021 Final Office Action dated Sep. 20, 2023.

U.S. Appl. No. 17/217,852, filed Mar. 30, 2021 Ex Parte Quayle Action dated Sep. 8, 2023.

U.S. Appl. No. 17/217,852, filed Mar. 30, 2021 Notice of Allowance dated Nov. 7, 2023.

U.S. Appl. No. 17/499,644, filed Oct. 12, 2021 Notice of Allowance dated Sep. 18, 2023.

U.S. Appl. No. 17/535,406, filed Nov. 24, 2021 Restriction Requirement dated Nov. 24, 2023.

U.S. Appl. No. 17/697,895, filed Mar. 17, 2022 Advisory Action dated Sep. 8, 2023.

U.S. Appl. No. 17/717,919, filed Apr. 11, 2022 Notice of Allowance dated Dec. 3, 2025.

U.S. Appl. No. 17/725,394, filed Apr. 20, 2022 Advisory Action dated Jan. 13, 2026.

U.S. Appl. No. 17/725,394, filed Apr. 20, 2022 Final Office Action dated Nov. 19, 2025.

U.S. Appl. No. 17/731,129, filed Apr. 27, 2022 Advisory Action dated Oct. 30, 2025.

U.S. Appl. No. 17/849,447, filed Jun. 24, 2022 Notice of Allowance dated Nov. 19, 2025.

U.S. Appl. No. 17/863,211, filed Jul. 12, 2022 Notice of Allowance dated Oct. 22, 2025.

U.S. Appl. No. 18/075,280, filed Dec. 5, 2022 Advisory Action dated Jan. 23, 2026.

U.S. Appl. No. 18/075,280, filed Dec. 5, 2022 Final Office Action dated Nov. 19, 2025.

U.S. Appl. No. 17/731,129, filed Apr. 27, 2022 Notice of Allowance dated Mar. 24, 2026.

U.S. Appl. No. 17/731,155, filed Apr. 27, 2022 Final Office Action dated Feb. 9, 2026.

U.S. Appl. No. 19/188,439, filed Apr. 24, 2025 Restriction Requirement dated Apr. 10, 2026.

* cited by examiner

EXTENDED FIBER OPTIC SENSING SYSTEM

PRIORITY

This application claims the benefit of priority to U.S. Provisional Application No. 63/175,449, filed Apr. 15, 2021, which is incorporated by reference in its entirety into this application.

BACKGROUND

In the past, certain intravascular guidance of medical instruments, such as guidewires and catheters for example, have used fluoroscopic methods for tracking tips of the medical instruments and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical instrument may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

In some instances, fiber optic shape sensing technology may be used to facilitate tracking of a medical instrument. Fiber optic 3D shape sensing involves localizing and quantifying deformation occurring at one or more locations along the length of a sensing region of an optical fiber. Such deformation may be a complex combination of bending, twisting, and axial elongation. In some instances, multiple reflective fiber Bragg gratings disposed along a sensing region may define reflected light characteristics consisting with the shape of the elongate device along the sensing region. An optical fiber may be defined to operate across a defined spectrum of light which in some instances may be limited. The spectrum is divided into spectral widths assigned to each grating along the optical fiber such that each grating operates across its spectral width.

Optical shape sensing via multiple fiber Bragg gratings disposed along a lengthy sensing region of an optical fiber (consistent with an elongate medical device) may suffer from competing operational characteristics. On one side, a high number of gratings along a sensing region may require the limited light spectrum to be divided up into narrow spectral widths thus limiting the degree of wavelength shift afforded to the grating. On the other side, a lower number of gratings increases the spacing distance between gratings where the instrument strain cannot be determined. As such there is a need to optically sense the shape of an elongate instrument without limiting the size of the spectral width and without increasing the spacing between gratings.

SUMMARY

Briefly summarized, disclosed herein is an elongate multi-core optical fiber instrument for insertion within a patient body. The multi-core optical fiber instrument includes a set of first optical fiber cores extending along a first sensing region of the multi-core optical fiber instrument, where each first optical fiber core includes a set of first sensors disposed along the first region. The multi-core optical fiber instrument further includes a set of second optical fiber cores extending along a second sensing region of the multi-core optical fiber instrument, where each second optical fiber core includes a set of second sensors disposed along the second sensing region. The first sensing region is located distal the second sensing region, and the first optical fiber cores extend along the second sensing region.

The set of first sensors is configured to operate across a set of first spectral widths of a light spectrum such that each first sensor of one first fiber core operates across a different spectral width from the other first sensors of the one first fiber core, and the set of second sensors is configured to operate across a set of second spectral widths of the light spectrum such that each second sensor of one second fiber core operates across a different spectral width from the other second sensors of the one second fiber core.

In some embodiments, the set of first spectral widths are the same for each first fiber core, and the set of second spectral widths are the same for each second fiber core. In some embodiments, the second spectral widths are a subset of the first spectral widths. In other embodiments, a majority of the set of second spectral widths are a subset of the first spectral widths and in still other embodiments, a substantial entirety of the second spectral widths are a subset of the first spectral widths.

The first sensors may be configured to determine one or more physical parameters of the multi-core optical fiber instrument along the first sensing region, and the second sensors may also be configured to determine the one or more physical parameters of the multi-core optical fiber instrument along the second sensing region. The physical parameters may include at least one of a bending direction, a shape, a torsional strain, a longitudinal strain, and a motion of the instrument.

The multi-core optical fiber instrument may define a circular cross section along the first region and one or more of the first optical fiber cores may be disposed adjacent a circumferential surface of the multi-core optical fiber instrument along the first region. In some embodiments, at least three of the first optical fiber cores are disposed adjacent the circumferential surface. The at least three first optical fiber cores may be equally spaced along the circumference surface. The at least three first optical fiber cores may extend along the first region at a constant angular position with respect to the multi-core optical fiber instrument. In some embodiments, the first sensors are equally spaced along the first sensing region defining a first separation distance.

The multi-core optical fiber instrument may define a circular cross section along the second sensing region, and one or more of the second optical fiber cores may be disposed adjacent a circumferential surface of the multi-core optical fiber instrument along the second region. In some embodiments, at least three of the second optical fiber cores are disposed adjacent the circumferential surface of the second region. The at least three second optical fiber cores may be equally spaced along the circumference surface of the second region and the at least three second optical fiber cores may extend along the second sensing region at a constant angular position with respect to the multi-core optical fiber instrument. In some embodiments, at least one of the at least three second optical fiber cores is disposed at the same angular position as one of the at least three first optical fiber cores. In some embodiments, each of the at least three second optical fiber cores is disposed at the same angular position as a separate one of the at least three first optical fiber cores. The second sensors may be equally spaced along the second sensing region defining a second separation distance and the second separation distance may be equal to the first separation distance. In some embodiments, the second sensing region at least partially overlaps the first sensing region. In some embodiments, at least one of the first optical fiber cores is disposed adjacent the circumferential surface along the second sensing region.

The multi-core optical fiber instrument may be incorporated into a medical device such as an introducer wire, a guidewire, a stylet, a probe, a sheath, a mesh, a tube, an obturator, or a catheter.

Also disclosed herein is a system for sensing one or more parameters experienced by an elongate medical device inserted within a patient body. The system includes an elongate multi-core optical fiber instrument and the elongate multi-core optical fiber instrument includes: (i) a set of first optical fiber cores extending along a first sensing region of the multi-core optical fiber instrument, where each first optical fiber core includes a set of first sensors disposed along the first sensing region, and (ii) a set of second optical fiber cores extending along a second sensing region of the multi-core optical fiber instrument, where each second optical fiber core includes a set of second sensors disposed along the second sensing region.

The system further includes a console including one or more processors and a non-transitory computer-readable medium having logic stored thereon. The logic when executed by the one or more processors, causes operations. The operations include providing an incident light signal to the multi-core optical fiber instrument, receiving reflected light signals from the first sensors across a set of first spectral widths, and receiving reflected light signals from the second sensors across a set of second spectral widths. In some embodiments, the second spectral widths are a subset of the first spectral widths.

The operations further include processing the reflected light signals associated with the first sensors and the second sensors so as to determine a shape of the multi-core optical fiber instrument along the first sensing region from reflected light associated with the first sensors and a shape of the multi-core optical fiber instrument along the second sensing region from reflected light associated with the second sensors. The operations also include causing a rendering on a graphical display of the shape of the multi-core optical fiber instrument along the first sensing region and the second sensing region.

The multi-core optical fiber instrument may further include a set of third optical fiber cores extending along a length of the multi-core optical fiber instrument, where each third optical fiber core comprising one or more third sensors disposed along the length of the multi-core optical fiber instrument. Each sensor is configured to determine a physiological parameter of the patient body, and the physiological parameter is one of a body temperature, a fluid flow rate, or a pulse oximetry.

In some embodiments, the multi-core optical fiber instrument is incorporated into one of an introducer wire, a guidewire, a stylet, a probe, a sheath, a mesh, a tube, an obturator, or a catheter.

Also disclosed herein is a medical system for sensing one or more parameters experienced by an elongate medical device inserted within a patient body. The system includes an elongate multi-core optical fiber instrument incorporated into the medical device, where the medical device is one of an introducer wire, a guidewire, a stylet, a probe, a sheath, a mesh, a tube, an obturator, or a catheter.

The multi-core optical fiber instrument includes a set of first optical fiber cores extending along a first sensing region of the multi-core optical fiber instrument, where each first optical fiber core includes a set of first sensors disposed along the first sensing region. The multi-core optical fiber instrument further includes a set of second optical fiber cores extending along a second sensing region of the multi-core optical fiber instrument, where each second optical fiber core includes a set of second sensors disposed along the second sensing region.

The system further includes a console including one or more processors and a non-transitory computer-readable medium having stored thereon logic that, when executed by the one or more processors, causes operations of the system. The operations include: (i) providing an incident light signal to the multi-core optical fiber instrument, (ii) receiving reflected light signals from the first sensors across a set of first spectral widths, and (iii) receiving reflected light signals from the second sensors across a set of second spectral widths, where the second spectral widths are a subset of the first spectral widths.

The operations further include: (i) processing the reflected light signals associated with the first sensors and the second sensors, (ii) determining a shape of the multi-core optical fiber instrument along the first sensing region from reflected light associated with the first sensors, (iii) determining a shape of the multi-core optical fiber instrument along the second sensing region from reflected light associated with the second sensors, and (iv) causing a rendering on a graphical display of the shape of the multi-core optical fiber instrument along the first sensing region and the second sensing region.

In some embodiments, the multi-core optical fiber instrument further includes one or more third optical fiber cores extending along the multi-core optical fiber instrument, where each third optical fiber core includes at least one third sensor. In such an embodiment, the logic, when executed by the one or more processors, further causes operations including: (i) receiving reflected light signals from the at least one third sensor across a first spectral width, (ii) determining a physiological parameter of the patient body from reflected light associated with the at least one third sensor, and (iii) causing a rendering on the graphical display depicting the physiological parameter along the multi-core optical fiber instrument in combination with the shape of the multi-core optical fiber instrument along the first sensing region and the second sensing region. The physiological parameter may be one of a body temperature, a blood flow rate, or a pulse oximetry.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Figure 1A:
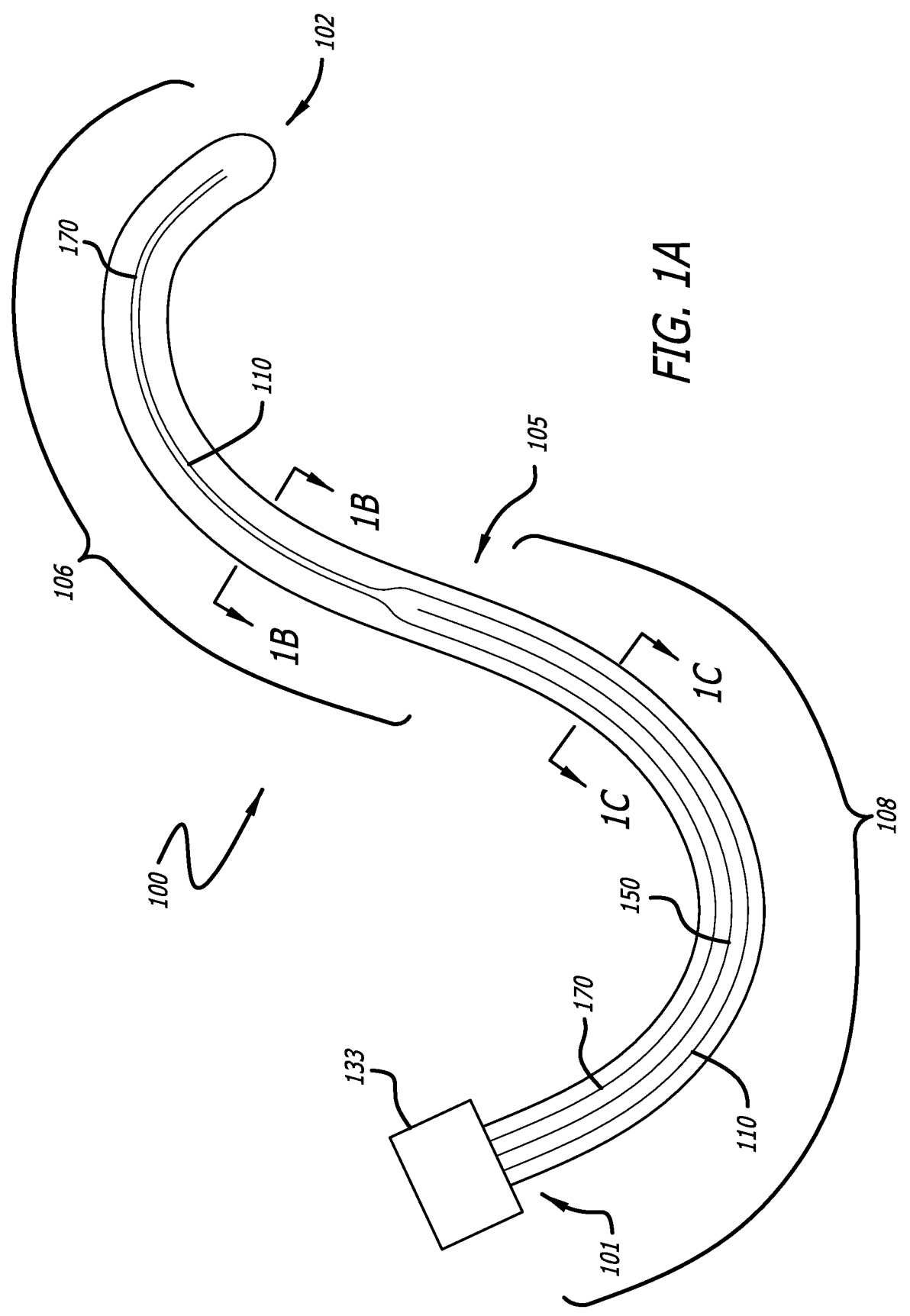
FIG. 1A is an illustrative embodiment of a multi-core optical fiber instrument with optical sensing capabilities, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

FIG. 1A is an illustrative embodiment of an elongate multi-core optical fiber instrument (instrument) 100 configured for insertion into a patient body, the instrument 100 defining a proximal end 101 and a distal end 102. The instrument 100 may be incorporated into a medical device. In some embodiments, the medical device may be vascular device such as a guidewire, a stylet, a catheter, or any other device configured for insertion into a vasculature of a patient. In other embodiments, the medical device may be a probe, a needle, a scope, biopsy device, or other device for insertion into a patient generally.

The instrument 100 may include multiple sets of optical fiber cores. The optical fiber cores are coupled to a fiber optic connector 133 at the proximal end 101 and extend along the instrument 100. The fiber cores may extend along an entire length of the instrument or a portion thereof. The various sets of optical fiber cores may define different sensing capabilities of the instrument 100. For example, one or more sets of optical fiber cores may be configured to determine one or more physical parameters of the instrument 100. The physical parameters may include a shape, a tensile strain, a compressive strain, a torsional strain, a curve, a bend radius, and a motion, for example. In some instances, sensing the shape of the instrument 100 may facilitate detection of an azygos blood vessel. Similarly, one or more sets of optical fiber cores may be configured to determine one or more physiological parameters of the patient body. Exemplary physiological parameters may include a temperature, a fluid flow rate or velocity, a motion of body tissue, and a pulse oximetry.

According to one embodiment, the instrument 100 includes a first sensing region 106 and a second sensing region 108 including a transition point 105 therebetween. The first sensing region 106 may extend between the distal end 102 and the transition point 105 and the second sensing region 108 may extend between the transition point 105 and the proximal end 101. In other embodiments, the instrument 100 may be divided into three or more sensing regions. In some embodiments, the first and second regions 106, 108 may partially overlap across the transition point 105. In the illustrated embodiment, each of the sensing regions 106, 108 is configured for determining a shape of the instrument 100 along the respective sensing region.

The shape sensing capability of the instrument 100 is provided via a set of first optical fiber cores 110 and a set of second optical fiber cores 150. In the illustrated embodiment, the first fiber cores 110 extend from the proximal end 101 to the distal end 102, and the second fiber cores 150 extend from the proximal end 101 to the transition point 105. As such, the first fiber cores 110 extend from the connector 133 through both the second sensing region 108 and the first sensing region 106. In some embodiments, the instrument 100 may include additional sets of optical fiber cores.

According to the illustrated embodiment, a set of third optical fiber cores 170 provides for a physiological parameter sensing capability along the instrument 100. The third fiber cores 170 extend along the length instrument 100.

Figure 1B:
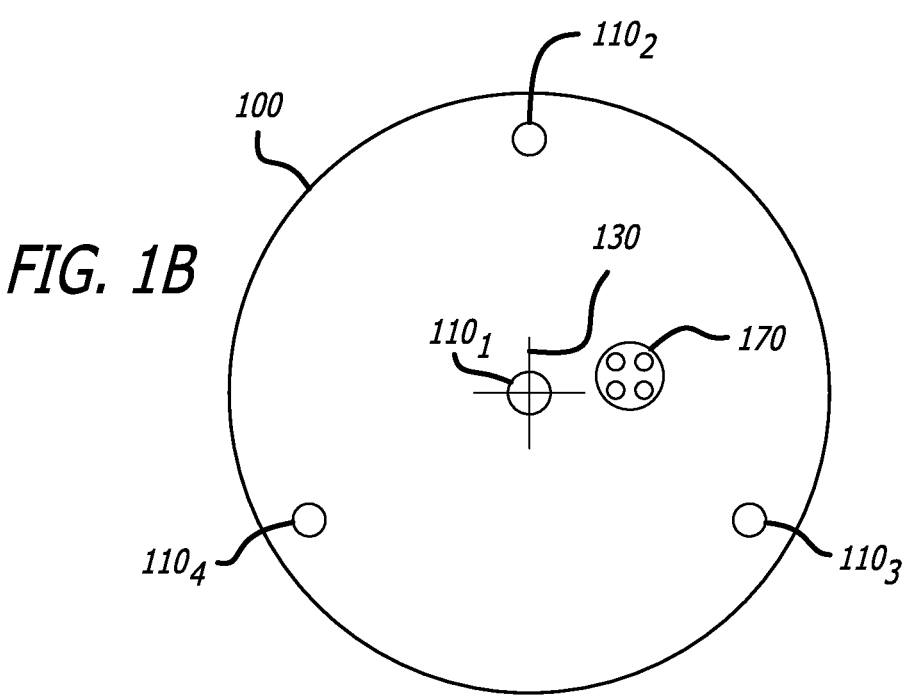
FIG. 1B illustrates cross section of a first sensing region of the multi-core optical fiber instrument of FIG. 1A, in accordance with some embodiments.

FIG. 1B illustrates a cross-section of the instrument 100 cut along sectioning lines 1B-1B across the first sensing region 106. As shown, the instrument 100 may define a circular cross section. As shown, the first fiber cores 110 include four optical fiber cores, i.e., fiber cores $110_1$-$101_4$. In other embodiments, the first fiber cores 110 may include less than four optical fiber cores or more than four optical fiber cores. The fiber core $110_1$ is disposed at a central axis 130 of the instrument 100 and the fiber cores $110_2$-$110_4$ are disposed adjacent a circumferential surface of the instrument 100. The fiber cores $110_2$-$110_4$ may be positioned substantially equidistant from each other as measured along a circumference of the instrument 100, such as at "top" (12 o'clock), "bottom-left" (8 o'clock) and "bottom-right" (4 o'clock) locations as shown. The third optical fiber cores 170 are also shown disposed within the cross section of the first sensing region 106.

Figure 1C:
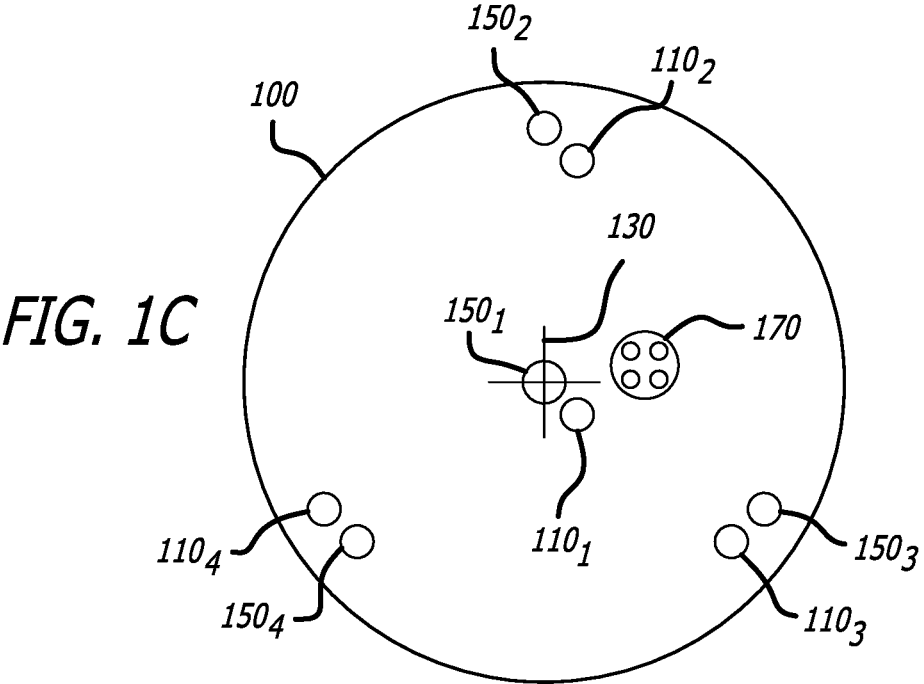
FIG. 1C illustrates cross section of a second sensing region of the multi-core optical fiber instrument of FIG. 1A, in accordance with some embodiments.

FIG. 1C illustrates a cross section of the instrument 100 cut along sectioning lines 1C-1C across the second sensing region 108. As shown, the fiber core $150_1$ is disposed at the central axis 130 of the instrument 100 and the fiber cores $150_2$-$150_4$ are disposed adjacent the circumferential surface of the instrument 100. The fiber cores $150_2$-$150_4$ may be positioned substantially equidistant from each other as measured along the circumference of the instrument 100, such as at "top" (12 o'clock), "bottom-left" (8 o'clock) and "bottom-right" (4 o'clock) locations as shown. Also shown are the fiber cores $110_1$-$110_4$ passing through the second sensing region 108 immediately adjacent the fiber cores $150_1$-$150_4$. As such, the fiber cores $110_1$ and $150_1$ may both be positioned substantially at the central axis 130 along the second sensing region 108. Similarly, the fiber cores $110_2$-$110_4$ and the fiber cores $150_2$-$150_4$ may also be positioned substantially at the "top" (12 o'clock), the "bottom-left" (8 o'clock) and the "bottom-right" (4 o'clock) locations, respectively along the second sensing region 108. The third optical fiber cores 170 are also shown disposed within the cross section of the second sensing region 108.

In an embodiment where the instrument 100 is incorporated within a tubular medical device, the fiber cores $110_2$-$110_4$ and the fiber cores $150_2$-$150_4$ may be disposed within a tubular wall. In such embodiments, the tubular medical device may include a rib extending through the central axis of the tubular device in which the fiber cores $110_1$, $150_1$ may be disposed.

Figure 2A:
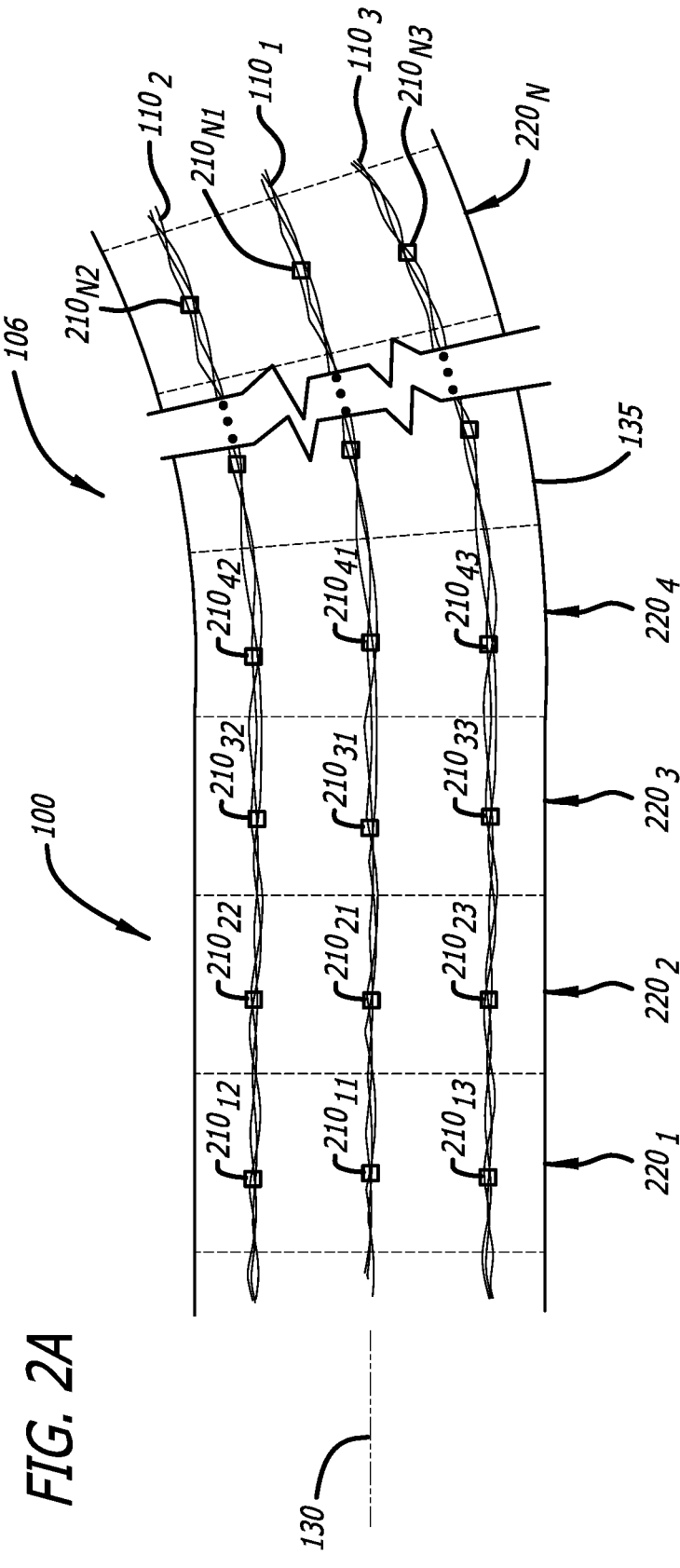
FIG. 2A is an exemplary embodiment of a structure of the first sensing region the multi-core optical fiber instrument of FIG. 1A, in accordance with some embodiments.

FIG. 2A is an exemplary embodiment of a structure of the first sensing region 106. The first sensing region 106 includes fiber cores $110_1$-$110_4$ (fiber core $110_4$ not shown) extending longitudinally along the first sensing region 106. As shown, the first sensing region 106 is subdivided into a plurality of cross-sectional regions $220_1$-$220_N$. Some or all of the cross-sectional regions $220_1$ . . . $220_N$ may be static (e.g., equal in length) or may be dynamic (e.g., vary in length among the regions $220_1$ . . . $220_N$). Each of the of cross-sectional regions $220_1$-$220_N$ includes a sensor 210 disposed within each of the fiber cores $110_1$-$110_4$ extending therethrough. In FIG. 2A, each of the sensors 210 includes a cross-sectional region designation "m" (m=1 . . . M) and a fiber designation "n" (n=1 . . . N) shown as $210_{mn}$. For example, sensor $210_{23}$ is located in the cross-sectional region $220_2$ and within fiber core $110_3$. The third optical fiber cores 170 extend along the first sensing region 106. However, the third optical fiber cores 170 are not shown in FIG. 2A for purposes of clarity.

Figure 2B:
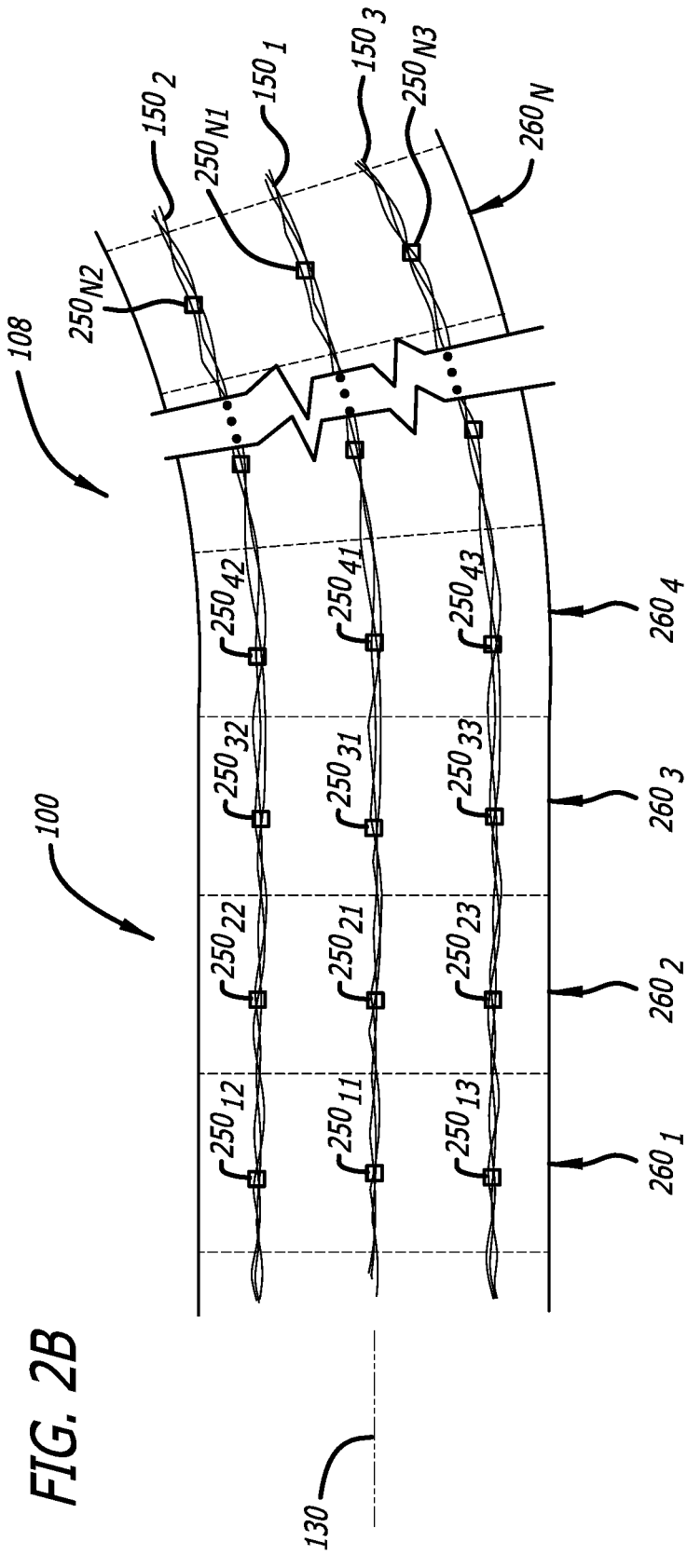
FIG. 2B is an exemplary embodiment of a structure of the second sensing region the multi-core optical fiber instrument of FIG. 1A, in accordance with some embodiments.

FIG. 2B is an exemplary embodiment of a structure of the second sensing region 108. The second sensing region 108 includes fiber cores $150_1$-$150_4$ ($150_4$ not shown) extending longitudinally along the second sensing region 108. First fiber cores $110_1$-$110_4$ (not shown for clarity purposes) also pass through the second sensing region 108. Similar to the first sensing region 106 as described above in relation to FIG. 2A, the second sensing region 108 is divided into a plurality of cross-sectional regions $260_1$-$260_N$. Some or all of the cross-sectional regions $260_1$ . . . $260_N$ may be static or dynamic as defined above. Each of the of cross-sectional regions $260_1$-$260_N$ includes a sensor 250 disposed within each of the fiber cores $150_1$-$150_4$ extending therethrough. The sensors 250 include a cross-sectional region designation "m" and a fiber designation "n" shown as $210_{mn}$. The fiber cores $110_1$-$110_4$ may simply pass through the second sensing region 108 and therefore, the cross-sectional regions $260_1$-$260_N$ do not include sensors 210 disposed within the fiber cores $110_1$-$110_4$. The third optical fiber cores 170 also extend along the second sensing region 108. However, the third optical fiber cores 170 are not shown in FIG. 2B for clarity purposes.

In some embodiments, the second sensing region 108 may form a proximal extension of the first sensing region 106, e.g., the first sensing region 106 and the second sensing region 108 may define the same or similar shape sensing characteristics. For example, as described above, the circumferential spacing of the second fiber cores $150_1$-$150_4$ along the second sensing region 108 may be consistent with the circumferential spacing of the first fiber cores $110_1$-$110_4$ along the first sensing region 106. In similar fashion, the cross-sectional regions $260_1$-$260_N$ may be consistent with the cross-sectional regions $220_1$-$220_N$.

In some embodiments, the cross-sectional regions $260_1$-$260_N$ may be different than the cross-sectional regions $220_1$-$220_N$. For example, the cross-sectional regions $220_1$-$220_N$ may be shorter than the cross-sectional regions $260_1$-$260_N$. A shorter cross-sectional region may define an enhanced parameter sensing resolution along the first sensing region 106. In some instances, an increased shape sensing resolution along the first sensing region 106 may be advantageous in embodiments where the instrument 100 is a vascular device configured to traverse blood vessels near the heart of the patient.

The instrument 100 is configured to operate across a spectrum of light (i.e., a range of light wavelength). More specifically, each optical fiber is configured to operate across the spectrum. The spectrum may be divided up into spectral widths (i.e., portions of the spectrum), where each spectral width defines a center wavelength. As discussed above, the sensors 210 and 250 may be reflective gratings such as fiber Bragg gratings (FBG), where each sensor along a single fiber is configured to reflect light within a defined different spectral width. For example, sensors $210_{11}$-$210_{N1}$ disposed along fiber core $110_1$ are configured to reflect light within different spectral widths of the spectrum. In some embodiments, the spectral widths defined for one optical fiber may be the same as the spectral widths defined for another optical fiber. For example, the sensors $210_{12}$-$210_{N2}$ disposed along fiber core $110_2$ may be configured to reflect light within the same spectral widths as sensors $210_{11}$-$210_{N1}$, respectively. In some embodiments, the defined spectral widths may be the same fiber cores as first fiber cores $110_1$-$110_4$, second fiber cores $150_1$-$150_4$, and third fiber cores 170.

As stated above, the sensors disposed within the different fiber cores $110_2$-$110_3$ but at the same cross-sectional regions $220_1$-$220_N$ may be configured to reflect incoming light at the same (or a substantially similar) center wavelength. As a result, the reflected light returns information that allows for a determination of one or more parameters according to a wavelength shift away from the center wavelength. For example, a strain (e.g., compression or tension) applied to an optical fiber (e.g., the fiber core $110_1$ along the first sensing region 106) results in a wavelength shift associated with the returned, reflected light. More specifically, a strain of the portion of the fiber core $110_1$ at the location of the sensor $210_{11}$ causes the wavelength of light reflected by the sensor $210_{11}$ to be shifted away from the center wavelength for the sensor 210*ii*. By way of general summary, a given sensor may reflect light at a wavelength shifted away from the defined center wavelength in accordance with a parameter experienced by the sensor.

According to one embodiment and by way of example, with respect to the first sensing region 106, in response to a curve of the instrument 100 toward the left direction (see FIG. 1B), the fiber core $110_4$ with the shortest radius in curved state would experience compressive strain (shortening). At the same time, the fiber core $110_3$ with the longest radius in the curved state would experience tensile strain (lengthening). As these strains are different, the reflected light from sensors $210_{n3}$ and $210_{n4}$ associated with the fiber cores $110_3$ and $110_4$ will reflect light having different shifts in wavelength. The differences in wavelength shift of the reflected light signals 152 can be used to determine the curve or shape of the instrument 100 corresponding to the wavelength shifts caused by the compressive strain and tensile strain for fiber cores $110_4$,$110_3$, respectively in comparison to the wavelength shift of the centrally located fiber core $110_1$.

Figure 2C:
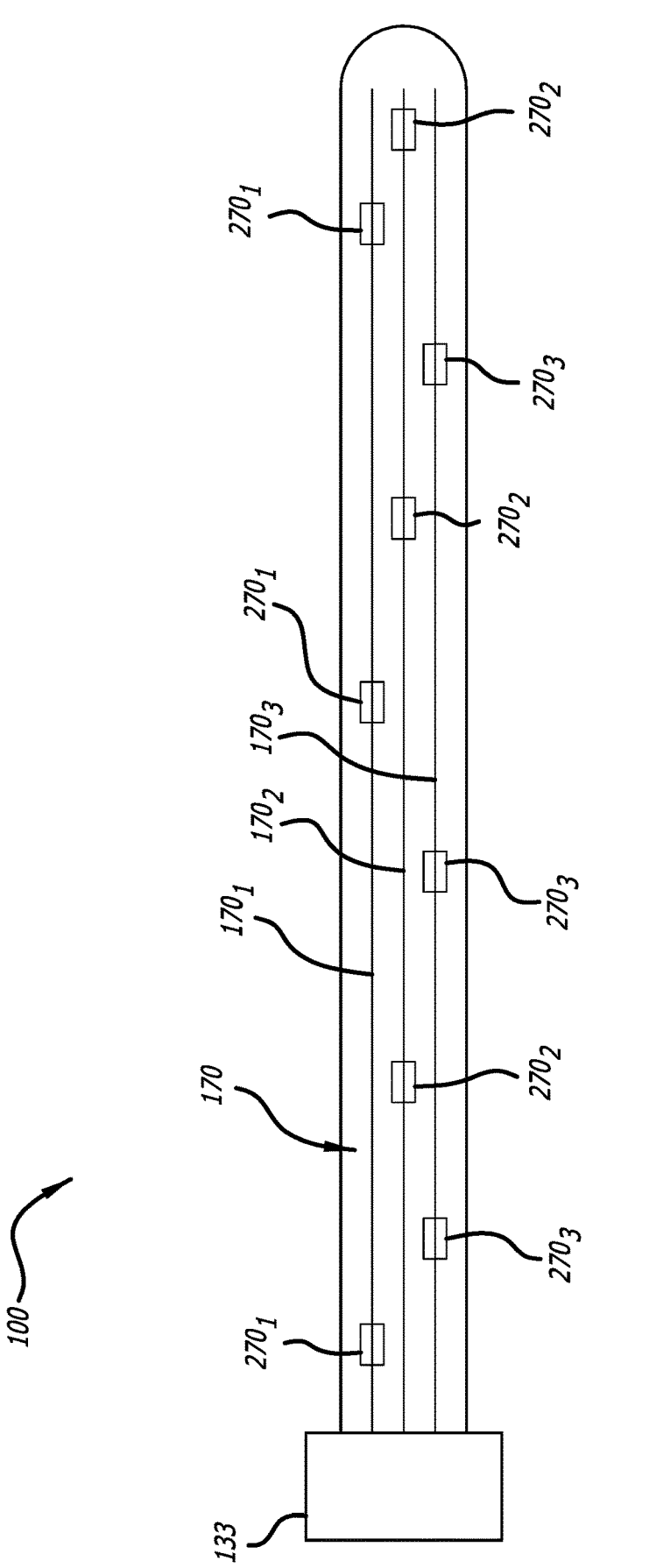
FIG. 2C is an exemplary embodiment of a structure of the multi-core optical fiber instrument of FIG. 1A illustrating a set of third optical fiber cores, in accordance with some embodiments.

FIG. 2C illustrates the set of third fiber cores 170 extending along the instrument 100 from the proximal end 101 to the distal end 102. As discussed above, the third fiber cores 170 may be configured to determine one or more physiological parameters of the patient body. In the illustrated exemplary embodiment, the set of third fiber cores 170 includes three fiber cores $170_1$, $170_2$, and $170_3$. In other embodiments, the set of third fiber cores 170 may include more or less than three fiber cores. The third fiber cores 170 extend through the first and second sensing regions 106, 108 as described above so as to determine physiological parameters along the first and second sensing regions 106, 108. In some embodiments, each third fiber 170 may be configured to determine a single physiological parameter. In other embodiments, each third fiber 170 may be configured to determine more than one physiological parameter. In still other embodiments, a physiological parameter may be determined by a combination of third fiber cores 170.

According to one embodiment, each of the third fiber cores 170 may determine a single physiological parameter as described below. The fiber $170_1$ may be configured to determine a temperature at various locations along the instrument 100. As such the fiber $170_1$ includes one or more sensors $270_1$ disposed at defined locations along the fiber $170_1$ where the sensors $270_1$ are configured to measure a temperature. The fiber $170_2$ may be configured to determine a blood flow rate at various locations along the instrument 100. As such the fiber $170_2$ includes one or more sensors 2702 disposed at defined locations along the fiber $170_2$ where the sensors 2702 are configured to measure a blood flow rate via a doppler effect, for example. The fiber $170_3$ may be configured to determine a pulse oximetry at various locations along the instrument 100. As such the fiber $170_3$ includes one or more sensors $270_s$ disposed at defined locations along the fiber $170_3$, where the sensors $270_3$ are configured to measure the pulse oximetry.

Figure 3:
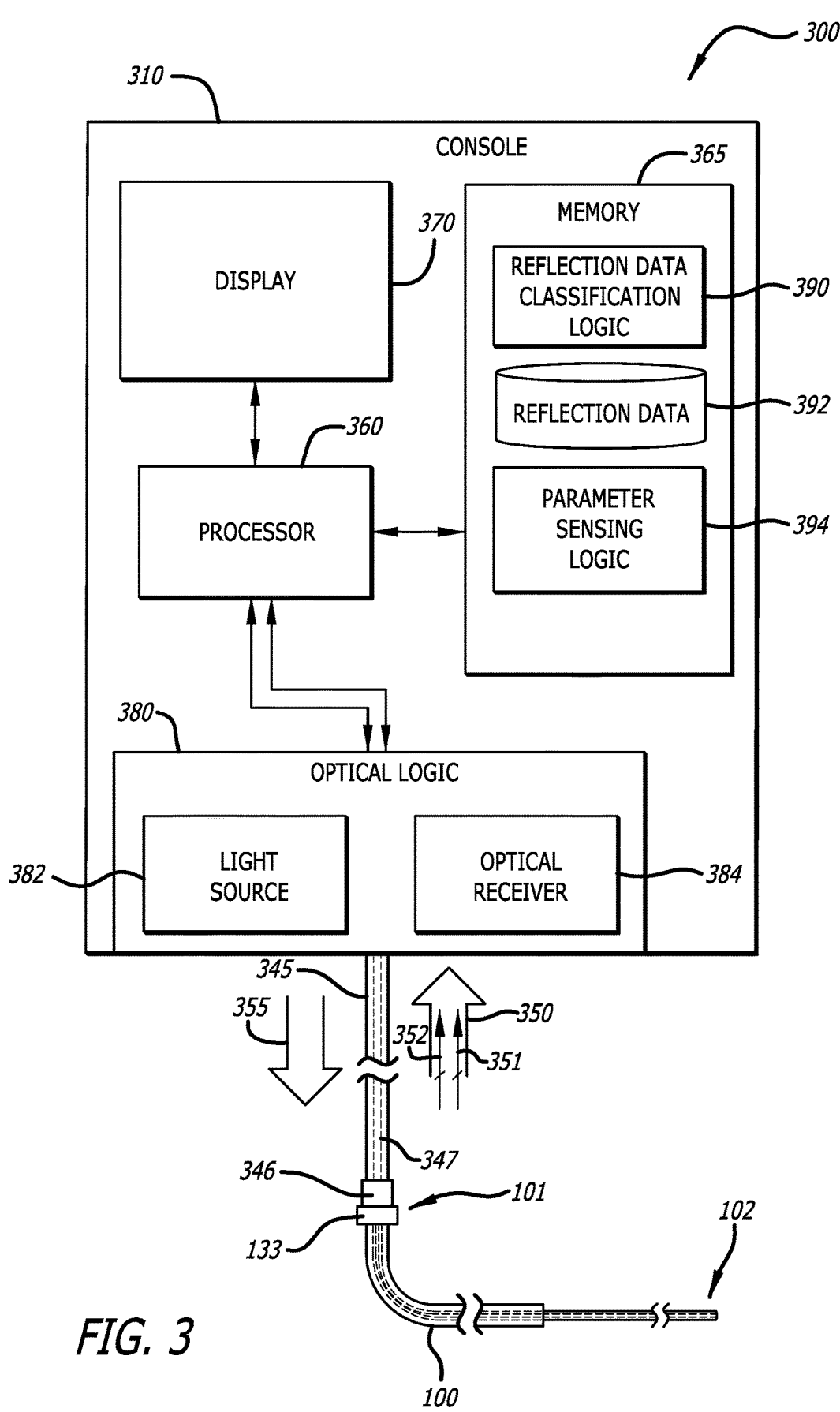
FIG. 3 is an illustrative embodiment of a medical device monitoring system including a multi-core optical fiber instrument with optic sensing capabilities, in accordance with some embodiments.

FIG. 3 is an illustrative embodiment of a medical system 300 including the instrument 100 for sensing parameters experienced by an elongate medical device inserted into a patient body. As shown, the system 300 generally includes a console 310 and the medical instrument 100 communicatively coupled with the console 310. The instrument 100 is incorporated into or coupled with an elongate medical device where the elongate medical device is one of an introducer wire, a guidewire, a stylet, a probe, a sheath, a mesh, a tube, an obturator, or a catheter.

The optical connector 133 enables the instrument 100 to be operably connected to the console 310 via an interconnect 345 including one or more interconnecting optical fiber cores 347. The connector 346 is configured to operatively couple with the optical connector 133 to allow for propagation of light between the console 310 and the instrument 100.

An exemplary implementation of the console 310 includes a processor 360, a memory 365, a display 370 and optical logic 380, although it is appreciated that the console 310 can take any one of a variety of forms and may include additional components (e.g., power supplies, ports, interfaces, etc.) that may facilitate operation of the console 310. The processor 360, with access to the memory 365 (e.g., non-volatile memory or non-transitory, computer-readable medium), is included to control functionality of the console 310 during operation. As shown, the display 370 may be a liquid crystal diode (LCD) display integrated into the console 310 and employed as a user interface to display information to the clinician during use. In another embodiment, the display 370 may be separate from the console 310. Although not shown, a user interface may be configured to provide user control of the console 310.

Referring still to FIG. 3, the optical logic 380 is configured to support operability of the instrument 100 including the return of information to the console 310, which information may facilitate determining the one or more parameters experienced by the instrument 100. Characteristics of reflected light signals 350 received at the console 310 from the instrument 100 correlate with the parameters experienced by the instrument 100. The characteristics may include shifts in wavelength caused by the parameters experienced by the instrument 100, as further described below. From information associated with the reflected light signals 350, the console 110 may determine (through computation or extrapolation of the wavelength shifts) the parameters experienced by the instrument 100.

According to one embodiment of the disclosure, as shown in FIG. 3, the optical logic 380 may include a light source 382 and an optical receiver 384. The light source 382 is configured to transmit the incident light 355 (e.g., broadband) for propagation over the interconnecting optical fiber cores 347 included in the interconnect 345, which are optically connected to the optical fiber cores 110, 150, 170 of the instrument 100. In one embodiment, the light source 382 is a tunable swept laser, although other suitable light sources can also be employed in addition to a laser, including semi-coherent light sources, LED light sources, etc.

The optical receiver 384 is configured to: (i) receive reflected optical signals 352 (reflected light signals) received from sensors fabricated within each of the fiber cores 110, 150, 170 of the instrument 100, and (ii) translate the reflected light signals 352 into reflection data 392, namely data in the form of electrical signals representative of the reflected light signals 352 including wavelength shifts caused by parameters determined by the instrument 100. Herein, the optical receiver 384 may be implemented as a multi-channel photodetector, such as a positive-intrinsic-negative "PIN" photodiode, avalanche photodiode, or the like.

As shown, both the light source 382 and the optical receiver 384 are operably connected to the processor 360, which governs their operation. Also, the optical receiver 384 is operably coupled to provide the reflection data 392 to the memory 365 for storage and processing by reflection data classification logic 390. The reflection data classification logic 390 may be configured to identify which reflection data 392 pertains to the first fiber cores 120, the second fiber cores 150, and the third fiber cores 170. The reflection data classification logic 390 may also identify the reflection data 392 pertaining to the sensors corresponding to the cross-sectional regions along the respective fiber cores. The reflection data 392 for each sensor is made available to parameter sensing logic 394 for analytics.

According to one embodiment of the disclosure, the parameter sensing logic 394 is configured to determine a shape of the instrument 100 along the first sensing region 106 via analysis of the reflected data 392 associated with the first optical fiber cores 120. Similarly, the parameter sensing logic 394 is configured to determine a shape of the instrument 100 along the second sensing region 108 via analysis of the reflected data 392 associated with the second optical fiber cores 150. From these analytics, the parameter sensing logic 194 may determine the shape of the instrument 100 (or more specifically the shape of the first and second sensing regions 106, 108) in 3D space for rendering on the display 370.

The parameter sensing logic 394 may also be configured to analyze reflection data 392 received from one or more sensors 270 disposed along the third optical fiber cores 170 to determine the physiological parameters of the patient body at the sensor locations along the instrument 100 for rendering on the display 370.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An elongate multi-core optical fiber instrument for insertion within a patient body, the instrument comprising:
   a set of first optical fiber cores extending along a first sensing region of the multi-core optical fiber instrument, each first optical fiber core comprising a set of first sensors disposed along the first region;
   a set of second optical fiber cores extending along a second sensing region of the multi-core optical fiber instrument, each second optical fiber core comprising a set of second sensors disposed along the second sensing region, wherein:
      the first sensing region is located distal the second sensing region,
      the first optical fiber cores extend along the second sensing region, and
      the second optical fiber cores extend from a proximal end of the multi-core optical fiber instrument and terminate at a transition point between the first sensing region and the second sensing region; and
   a set of third optical fiber cores extending along a length of the multi-core optical fiber instrument, each third optical fiber core comprising a set of third sensors disposed along the length of the multi-core optical fiber instrument, wherein the third sensors are configured to determine a physiological parameter of the patient body, and wherein the physiological parameter is one of a body temperature, a fluid flow rate, or a pulse oximetry.

2. The multi-core optical fiber instrument of claim 1, wherein:
   the set of first sensors is configured to operate across a set of first spectral widths of a light spectrum such that each first sensor of one first fiber core operates across a different spectral width from the other first sensors of the one first fiber core, and
   the set of second sensors is configured to operate across a set of second spectral widths of the light spectrum such that each second sensor of one second fiber core operates across a different spectral width from the other second sensors of the one second fiber core.

3. The multi-core optical fiber instrument of claim 2, wherein the set of first spectral widths are the same for each first fiber core, and the set of second spectral widths are the same for each second fiber core.

4. The multi-core optical fiber instrument of claim 2, wherein a portion of the second spectral widths are a subset of the first spectral widths.

5. The multi-core optical fiber instrument of claim 2, wherein a majority of the set of second spectral widths are a subset of the first spectral widths.

6. The multi-core optical fiber instrument of claim 2, wherein a substantial entirety of the second spectral widths are a subset of the first spectral widths.

7. The multi-core optical fiber instrument of claim 1, wherein:
   the first sensors are configured to determine one or more physical parameters of the multi-core optical fiber instrument along the first sensing region, and
   the second sensors are configured to determine the one or more physical parameters of the multi-core optical fiber instrument along the second sensing region.

8. The multi-core optical fiber instrument of claim 7, wherein the one or more physical parameters comprise at least one of a bending direction, a shape, torsional strain, longitudinal strain, and a motion of the multi-core optical fiber instrument.

9. The multi-core optical fiber instrument of claim 1, wherein the multi-core optical fiber instrument defines a circular cross section along the first sensing region.

10. The multi-core optical fiber instrument of claim 9, wherein one or more of the first optical fiber cores are disposed adjacent a circumferential surface of the multi-core optical fiber instrument along the first sensing region.

11. The multi-core optical fiber instrument of claim 10, wherein at least three of the first optical fiber cores are disposed adjacent the circumferential surface.

12. The multi-core optical fiber instrument of claim 11, wherein the at least three first optical fiber cores are equally spaced along the circumference surface.

13. The multi-core optical fiber instrument of claim 11, wherein the at least three first optical fiber cores extend along the first sensing region at a constant angular position with respect to the instrument.

14. The multi-core optical fiber instrument of claim 1, wherein the first sensors are equally spaced along the first sensing region defining a first separation distance.

15. The multi-core optical fiber instrument of claim 1, wherein the multi-core optical fiber instrument defines a circular cross section along the second sensing region, and wherein one or more of the second optical fiber cores are disposed adjacent a circumferential surface of the multi-core optical fiber instrument along the second sensing region.

16. The multi-core optical fiber instrument of claim 15, wherein at least three of the second optical fiber cores are disposed adjacent the circumferential surface of the second sensing region.

17. The multi-core optical fiber instrument of claim 16, wherein the at least three second optical fiber cores are equally spaced along the circumference surface of the second sensing region.

18. The multi-core optical fiber instrument of claim 16, wherein the at least three second optical fiber cores extend along the second sensing region at a constant angular position with respect to the multi-core optical fiber instrument.

19. The multi-core optical fiber instrument of claim 16, wherein at least one of the at least three second optical fiber cores is disposed at the same angular position as one of the at least three first optical fiber cores.

20. The multi-core optical fiber instrument of claim 16, wherein each of the at least three second optical fiber cores is disposed at the same angular position as a separate one of the at least three first optical fiber cores.

21. The multi-core optical fiber instrument of claim 1, wherein the second sensors are equally spaced along the second sensing region defining a second separation distance.

22. The multi-core optical fiber instrument of claim 21, wherein second separation distance is equal to the first separation distance.

23. The multi-core optical fiber instrument of claim 1, wherein the second sensing region at least partially overlaps the first sensing region.

24. The multi-core optical fiber instrument of claim 23, wherein at least one of the first optical fiber cores is disposed adjacent the circumferential surface along the second sensing region.

25. The multi-core optical fiber instrument of claim 1, wherein the multi-core optical fiber instrument is incorporated into one of an introducer wire, a guidewire, a stylet, a probe, a sheath, a mesh, a tube, an obturator, or a catheter.

26. A medical system for sensing one or more parameters experienced by an elongate medical device inserted within a patient body, the system comprising:

an elongate multi-core optical fiber instrument comprising:

a set of first optical fiber cores extending along a first sensing region of the multi-core optical fiber instrument, each first optical fiber core comprising a set of first sensors disposed along the first sensing region;

a set of second optical fiber cores extending along a second sensing region of the multi-core optical fiber instrument, each second optical fiber core comprising a set of second sensors disposed along the second sensing region, wherein:

the multi-core optical fiber instrument is incorporated into the elongate medical device, the medical device is one of an introducer wire, a guidewire, a stylet, a probe, a sheath, a mesh, a tube, an obturator, or a catheter;

the first sensing region is located distal the second sensing region, the first optical fiber cores extend along the second sensing region, and the second optical fiber cores extend from a proximal end of the multi-core optical fiber instrument and terminate at a transition point between the first sensing region and the second sensing region;

a set of third optical fiber cores extending along a length of the multi-core optical fiber instrument, each third optical fiber core comprising a set of third sensors disposed along the length of the multi-core optical fiber instrument, wherein the third sensors are configured to determine a physiological parameter of the patient body; and a console including one or more processors and a non-transitory computer-readable medium having stored thereon logic that, when executed by the one or more processors, causes operations including:

providing an incident light signal to the multi-core optical fiber instrument, receiving reflected light signals from the first sensors across a set of first spectral widths, receiving reflected light signals from the second sensors across a set of second spectral widths, the second spectral widths being a subset of the first spectral widths, receiving reflected light signals from the third sensors across the first spectral width, processing the reflected light signals associated with the first sensors, and the second sensors, and the third sensors, determining a shape of the multi-core optical fiber instrument along the first sensing region from reflected light associated with the first sensors, determining a shape of the multi-core optical fiber instrument along the second sensing region from reflected light associated with the second sensors, determining a physiological parameter of the patient body from reflected light associated with the third sensors, and causing a rendering on a graphical display depicting the physiological parameter along the multi-core optical fiber instrument in combination with the shape of the multi-core optical fiber instrument along the first sensing region and the second sensing region.

27. The system of claim 26, wherein the physiological parameter is one of a body temperature, a blood flow rate, or a pulse oximetry.

\* \* \* \* \*